United States Patent
Noguchi et al.

(10) Patent No.: US 10,028,726 B2
(45) Date of Patent: Jul. 24, 2018

(54) ULTRASOUND DIAGNOSTIC APPARATUS

(71) Applicant: FUJIFILM Corporation, Tokyo (JP)

(72) Inventors: Masafumi Noguchi, Ashigara-kami-gun (JP); Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 167 days.

(21) Appl. No.: 14/094,452

(22) Filed: Dec. 2, 2013

(65) Prior Publication Data

US 2014/0088424 A1    Mar. 27, 2014

Related U.S. Application Data

(63) Continuation of application No. PCT/JP2012/063941, filed on May 30, 2012.

(30) Foreign Application Priority Data

Jun. 3, 2011   (JP) .................................. 2011-125233

(51) Int. Cl.
*A61B 8/08* (2006.01)
*A61B 8/00* (2006.01)
(Continued)

(52) U.S. Cl.
CPC ............ *A61B 8/485* (2013.01); *A61B 8/0891* (2013.01); *A61B 8/14* (2013.01); *A61B 8/486* (2013.01);
(Continued)

(58) Field of Classification Search
None
See application file for complete search history.

(56) References Cited

U.S. PATENT DOCUMENTS 4,420,000 A * 12/1983 Bailey .................... A61B 5/024
                                                        600/519
5,840,028 A    11/1998 Chubachi et al.
(Continued)

FOREIGN PATENT DOCUMENTS

| JP | 10-5226 A | 1/1998 |
|---|---|---|
| JP | 2006-184058 A | 7/2006 |

(Continued)

OTHER PUBLICATIONS

Peter R. Hoskins, Kevin Martin, Abigail Thrush, "Diagnostic Ultrasound: Physics and Equipment", Cambridge University Press, Jun. 17, 2010.*
(Continued)

*Primary Examiner* — Amelie R Gillman
*Assistant Examiner* — Carolyn Pehlke
(74) *Attorney, Agent, or Firm* — Birch, Stewart, Kolasch & Birch, LLP

(57) ABSTRACT

Provided is an ultrasound diagnostic apparatus that measures an elastic modulus of a vascular wall, the apparatus allowing selection of a heartbeat suitable for the measurement of the elastic modulus. The problem is solved by storing M-mode images at predetermined intervals in the azimuth direction in a B-mode image, selecting a position in the azimuth direction in the B-mode image, and displaying the M-mode image of the selected position together with the B-mode image.

5 Claims, 13 Drawing Sheets

(51) Int. Cl.
    *A61B 8/14*    (2006.01)
    *G01S 7/52*    (2006.01)
    *G06T 7/00*    (2017.01)
(52) U.S. Cl.
    CPC .......... *A61B 8/5207* (2013.01); *A61B 8/5284* (2013.01); *G01S 7/52042* (2013.01); *G01S 7/52066* (2013.01); *A61B 8/4405* (2013.01); *G06T 7/0012* (2013.01)

(56) References Cited

U.S. PATENT DOCUMENTS

| | | | | |
|---|---|---|---|---|
| 6,350,238 | B1* | 2/2002 | Olstad | A61B 8/00 600/437 |
| 2005/0197572 | A1* | 9/2005 | Williams | A61B 8/06 600/437 |
| 2007/0038086 | A1* | 2/2007 | Ohtsuka | 600/437 |
| 2007/0161898 | A1* | 7/2007 | Hao | A61B 8/488 600/443 |
| 2008/0221450 | A1* | 9/2008 | Kim | A61B 8/08 600/443 |
| 2010/0113930 | A1 | 5/2010 | Miyachi | |
| 2010/0210948 | A1* | 8/2010 | Nishimura | 600/454 |
| 2010/0298701 | A1* | 11/2010 | Shin | A61B 8/00 600/437 |

FOREIGN PATENT DOCUMENTS

| | | |
|---|---|---|
| JP | 2010-233956 A | 10/2010 |
| JP | 2011-19993 A | 2/2011 |

OTHER PUBLICATIONS

Ketterling, Jeffrey, Orlando Aristizabal, and Daniel H. Turnbull. "ECG-gated imaging of a mouse heart using a 40-MHz annular array." Ultrasonics Symposium, 2008. IUS 2008. IEEE. IEEE, 2008.*

PCT/ISA/210—International Search Report dated Jun. 26, 2012, issued in PCT/JP2012/063941.

Chinese Office Action and Search Report, dated Nov. 18, 2014, for Chinese Application No. 201280026478.0, including English translation.

Extended European Search Report dated Oct. 20, 2014, issued in corresponding European Patent Application No. 12793419.8.

* cited by examiner

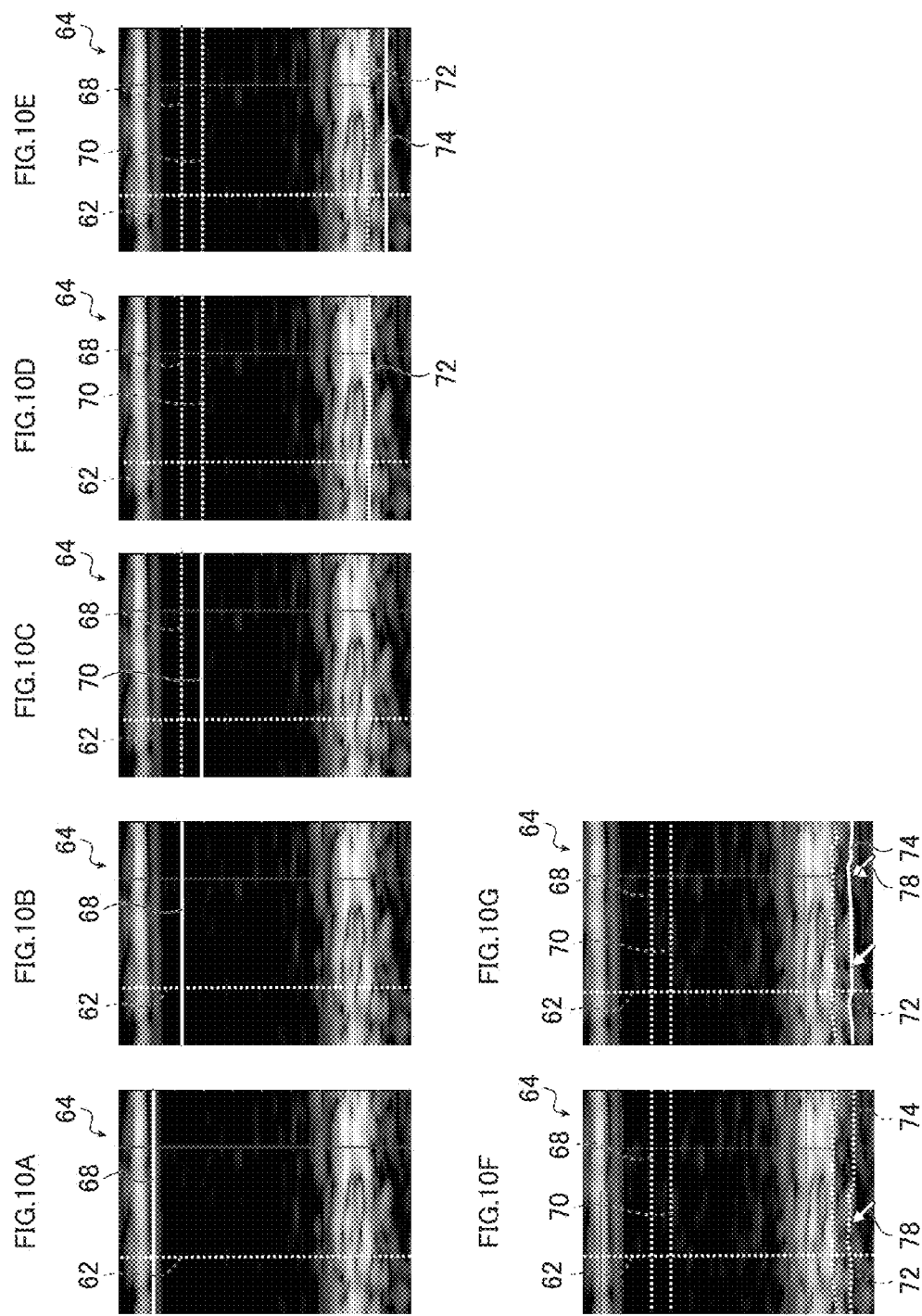

ULTRASOUND DIAGNOSTIC APPARATUS

CROSS REFERENCE TO RELATED APPLICATIONS

This application is a Continuation Application of PCT/JP2012/063941 filed on May 30, 2012, which claims priority under 35 U.S.C 119(a) to Patent Application No. 2011-125233 filed in Japan on Jun. 3, 2011, all of which are hereby expressly incorporated by reference into the present application.

BACKGROUND OF THE INVENTION

The present invention relates to an ultrasound diagnostic apparatus suitable for measuring an elastic modulus of a vascular wall. In particular, the present invention relates to an ultrasound diagnostic apparatus that allows selection of a favorable heartbeat which enables accurate measurement of an elastic modulus of a vascular wall.

Ultrasound diagnostic apparatuses using ultrasound images are put to practical use in the medical field.

In general, this type of ultrasound diagnostic apparatus has an ultrasound probe (hereinafter referred to as a probe) and a diagnostic apparatus body. The ultrasound diagnostic apparatus transmits ultrasonic waves from the probe into a subject's body, receives an ultrasonic echo from the subject's body with the probe, and electrically processes the resulting reception signals in the diagnostic apparatus body to produce an ultrasound image.

Also, ultrasonic waves are transmitted toward a blood vessel, a cardiac wall, or the like, an ultrasonic echo therefrom is received, a reception signal is analyzed to obtain an amount of displacement of a vascular wall or the like, and based on the displacement amount, the elastic modulus of the vascular wall, the cardiac wall (heart muscle) or the like is measured.

For example, JP 10-5226 A describes that ultrasonic waves are transmitted and received to and from an object moving in synchronization with heartbeats (cardiac pulsation) to obtain a reception signal of an ultrasonic echo, the instantaneous position of the object is determined based on the amplitude and phase of the reception signal, and the large amplitude displacement motion of the vascular wall based on the heartbeats is tracked, thereby obtaining the elastic modulus of the blood vessel.

Specifically, a motion velocity waveform of minute vibration of the vascular wall is obtained based on a sequential position of the vascular wall, a tracking trajectory of each of sections given at predetermined intervals in the depth direction in the vascular wall is obtained, and a temporal change in thickness of each section is calculated to obtain the elastic modulus of the blood vessel.

JP 2010-233956 A also describes an ultrasound diagnostic apparatus which obtains an amount of displacement of a blood vessel or the like from a reception signal of an ultrasonic echo obtained by transmitting and receiving ultrasonic waves to and from an object moving in synchronization with heartbeats, and obtains an elastic modulus from the displacement amount.

In this ultrasound diagnostic apparatus, a B-mode image and an M-mode image are produced using a reception signal obtained from an object such as a blood vessel, blurring due to hand or body movement is detected from the reception signal for the M-mode image, a positional variation of the probe and the subject is detected using the reception signal of the M-mode image where the blurring is detected, the accuracy of the reception signal is determined from the detection result, an amount of displacement of the object is obtained using the reception signal of the M-mode image whose accuracy is determined to be high, and the elastic modulus of the vascular wall or the like is measured from the displacement amount.

SUMMARY OF THE INVENTION

In order to accurately measure an elastic modulus of a blood vessel or the like based on such a displacement amount of an object moving in synchronization with heartbeats, the analysis needs to be performed with an M-mode image which has a heartbeat suitable for analysis and is less affected by blurring due to hand movement of the tester or body movement of the subject, irregular heartbeats, speckles (speckle noise or speckle pattern) or the like.

Accordingly, for instance, the ultrasound diagnostic apparatus stated in JP 2010-233956 A detects blurring due to hand movement of the tester or body movement of the subject and measures the elastic modulus from the displacement amount of the vascular wall or the like using the reception signal of the heartbeat which is not affected by the blurring due to hand movement and has high accuracy.

However, in a conventional ultrasound diagnostic apparatus capable of performing a so-called B/M mode display, only an M-mode image of a predetermined line (at a predetermined position in the azimuth direction) set in a B-mode image is displayed.

Therefore, the displayed M-mode image does not necessarily include an M-mode image of a heartbeat which is not affected by blurring due to hand movement, speckles, or the like and thus suitable for analysis.

An object of the invention is to solve the problem of the prior art and to provide an ultrasound diagnostic apparatus which can select a heartbeat most suitable for analysis from among heartbeats in an M-mode image, thereby performing accurate measurement of an elastic modulus of a vascular wall using an amount of displacement of the vascular wall or the like in the M-mode image, as well as other operations.

In order to attain the foregoing object, an ultrasound diagnostic apparatus according to the present invention comprises an ultrasound probe which has ultrasound transducers transmitting ultrasonic waves, receiving an ultrasonic echo reflected by a subject, and outputting a reception signal according to the received ultrasonic echo; an image producing unit adapted to produce a B-mode image as well as M-mode images over an entire region along an azimuth direction in the B-mode image from the reception signal output from the ultrasound transducers; a storage unit adapted to store the M-mode images produced by the image producing unit; a display; a display processing unit adapted to display on the display at least one of the B-mode image produced by the image producing unit and an M-mode image stored in the storage unit; and a position selection instructing unit adapted to select a position in the azimuth direction in the B-mode image displayed on the display, wherein when a position in the azimuth direction in the B-mode image displayed on the display is selected by the position selection instructing unit, the display processing unit reads out from the storage unit an M-mode image corresponding to the selected position and displays the M-mode image along with the B-mode image on the display.

In the ultrasound diagnostic apparatus as described above, it is preferred to have a heartbeat detecting unit adapted to detect a heartbeat in the M-mode image, wherein the display processing unit displays all of heartbeats detected by the heartbeat detecting unit in a displayed M-mode image.

It is preferred to have a heartbeat selection instructing unit adapted to select a heartbeat displayed in the M-mode image. Preferably, the position selection instructing unit doubles as the heartbeat selection instructing unit.

It is preferred to have a position adjustment instructing unit adapted to adjust a position of the heartbeat selected by the heartbeat selection instructing unit. Preferably, the position selection instructing unit doubles as the position adjustment instructing unit.

It is preferred to have a heartbeat extracting unit adapted to, in response to selection of a heartbeat by the heartbeat selection instructing unit, extract a heartbeat corresponding to a heartbeat selected in the displayed M-mode image from all of M-mode images stored in the storage unit.

It is preferred to have a region-of-interest setting instructing unit adapted to set a region of interest in a B-mode image displayed on the display.

Preferably, when a region of interest is set by the region-of-interest setting instructing unit, the image producing unit produces a B-mode image of the region of interest and M-mode images over an entire region of the region of interest along the azimuth direction; and when a region of interest is set by the region-of-interest setting instructing unit, the display processing unit displays the B-mode image of the region of interest and an M-mode image of a predetermined position in the azimuth direction in the B-mode image on the display.

Preferably, a frame rate of ultrasonic waves transmitted by the ultrasound transducers is increased in response to an instruction to set the region of interest to be higher than before the instruction to set the region of interest.

The ultrasound diagnostic apparatus of the invention having the foregoing configuration stores not only an M-mode image of a predetermined position in the azimuth direction in a B-mode image but also M-mode images over the entire region along the azimuth direction in the B-mode image, and selects a position in the B-mode image, whereby it becomes possible to read out from the storage unit an M-mode image of an arbitrary position in the azimuth direction and display it.

Therefore, according to the ultrasound diagnostic apparatus of the invention, from among the stored M-mode images, the M-mode image of the heartbeat that is most suitable for analysis can be selected. Therefore, according to the invention, in the ultrasound diagnostic apparatus, the heartbeat most suitable for analysis can be selected to perform the measurement of an elastic modulus of a vascular wall or the like, thereby enabling to steadily perform accurate measurement.

BRIEF DESCRIPTION OF THE DRAWINGS

FIGS. 10A to 10G are conceptual diagrams each showing an example of image display in the ultrasound diagnostic apparatus shown in FIG. 1.

DETAILED DESCRIPTION OF THE INVENTION

An ultrasound diagnostic apparatus of the invention is described in detail below with reference to the preferred embodiments shown in the accompanying drawings.

Figure 1:
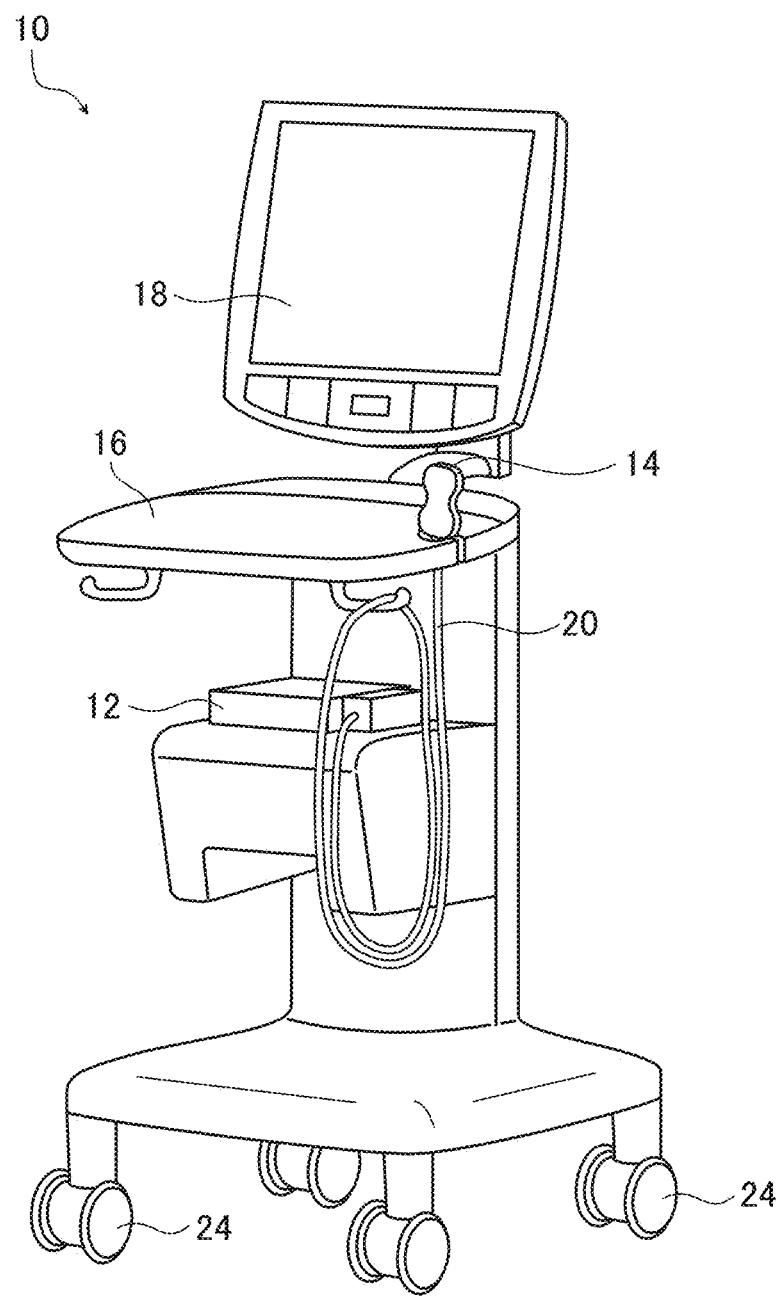
FIG. 1 is a diagram conceptually showing an example of an ultrasound diagnostic apparatus of the invention.

FIG. 1 conceptually shows the appearance of an example of the ultrasound diagnostic apparatus of the invention.

As shown in FIG. 1, an ultrasound diagnostic apparatus 10 basically has a diagnostic apparatus body 12, an ultrasound probe 14, an operating panel 16, and a display 18. Casters 24 are arranged at the bottom of the ultrasound diagnostic apparatus 10 so that the apparatus can be easily moved by human power.

The ultrasound probe 14 (hereinafter referred to as a probe 14) performs transmission and reception of ultrasonic waves, and supplies a reception signal according to a received ultrasonic echo to the diagnostic apparatus body 12.

The probe 14, which is a known ultrasound probe used in various ultrasound diagnostic apparatuses, has so-called ultrasound transducers (ultrasonic piezoelectric elements) arranged in a one-dimensional or two-dimensional array which transmit ultrasonic waves toward a subject, receive an ultrasonic echo reflected by the subject, and output an electrical signal (reception signal) according to the received ultrasonic echo.

In the invention, the type of the probe 14 is not particularly limited, and various types such as a convex type, a linear type and a sector type may be used. An external probe or a radial scan type probe for use in an ultrasound endoscope may be used. In addition, the probe 14 may have an ultrasound transducer compatible with harmonic imaging for use in receiving second or higher order harmonics of transmitted ultrasonic waves.

In the illustrated example, the probe 14 and the diagnostic apparatus body 12 are interconnected by a cable 20. However, the invention is not limited thereto. A transmission circuit 28, a reception circuit 30, a transmission/reception control unit 32, and the like described below may be arranged in the probe 14, and the probe 14 and the diagnostic apparatus body 12 may be interconnected by wireless communication.

The display 18 is a known display (display device).

In the ultrasound diagnostic apparatus 10, as in various ultrasound diagnostic apparatuses, the display 18 displays an ultrasound image according to a reception signal output from the probe 14, information of the subject, selecting means and instructing means for operation through a GUI (Graphical User Interface), a region of interest (hereinafter abbreviated as ROI), an elasticity measurement result of a vascular wall to be described below, and the like.

The operating panel 16 is provided to operate the ultrasound diagnostic apparatus 10.

Although not illustrated, in the ultrasound diagnostic apparatus 10, the operating panel 16 has arranged therein selecting means for selecting various modes such as a B mode and an M mode, a trackball (track pad/touch pad) for moving a cursor, a line, or the like displayed on the display 18, a set button for determining (confirming) selection or operation, a freeze button for switching between motion image display and still image display, changing means for changing a depth of field of an ultrasound image, gain adjusting means, a zoom button for enlarging an ultrasound image, and the like.

In the ultrasound diagnostic apparatus 10, as the modes, in addition to modes of a common ultrasound diagnostic apparatus such as a B mode and an M mode, a VE mode (Vascular Elasticity mode) for measuring an elastic modulus of a vascular wall is also set.

Figure 6A:
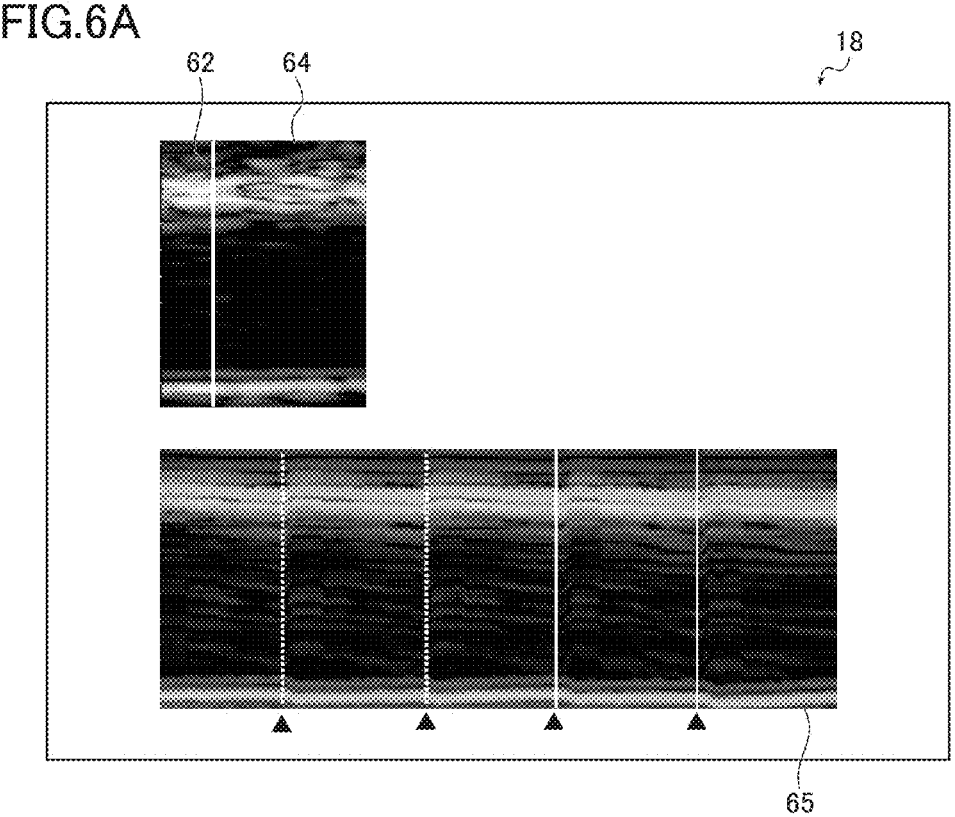
FIGS. 6A and 6B are conceptual diagrams each showing an example of image display in the ultrasound diagnostic apparatus shown in FIG. 1.
Figure 6B:
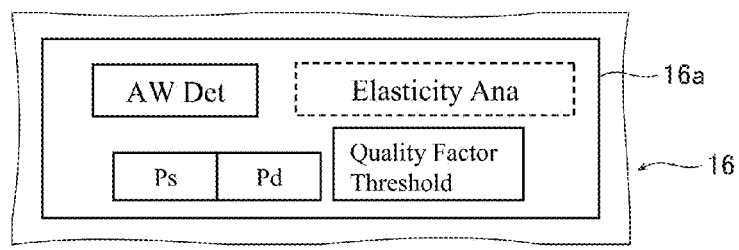

Although not illustrated again, the operating panel 16 also has arranged therein a touch panel 16a which is a display device for operation through the GUI (see FIG. 6B).

The diagnostic apparatus body 12 controls the overall operation of the ultrasound diagnostic apparatus 10 and produces an ultrasound image according to a reception signal output from the probe 14 to be displayed on the display 18, as well as performing various processes for measuring a blood vessel elastic modulus. The diagnostic apparatus body 12 is constituted using, for example, a computer or the like.

Figure 2:
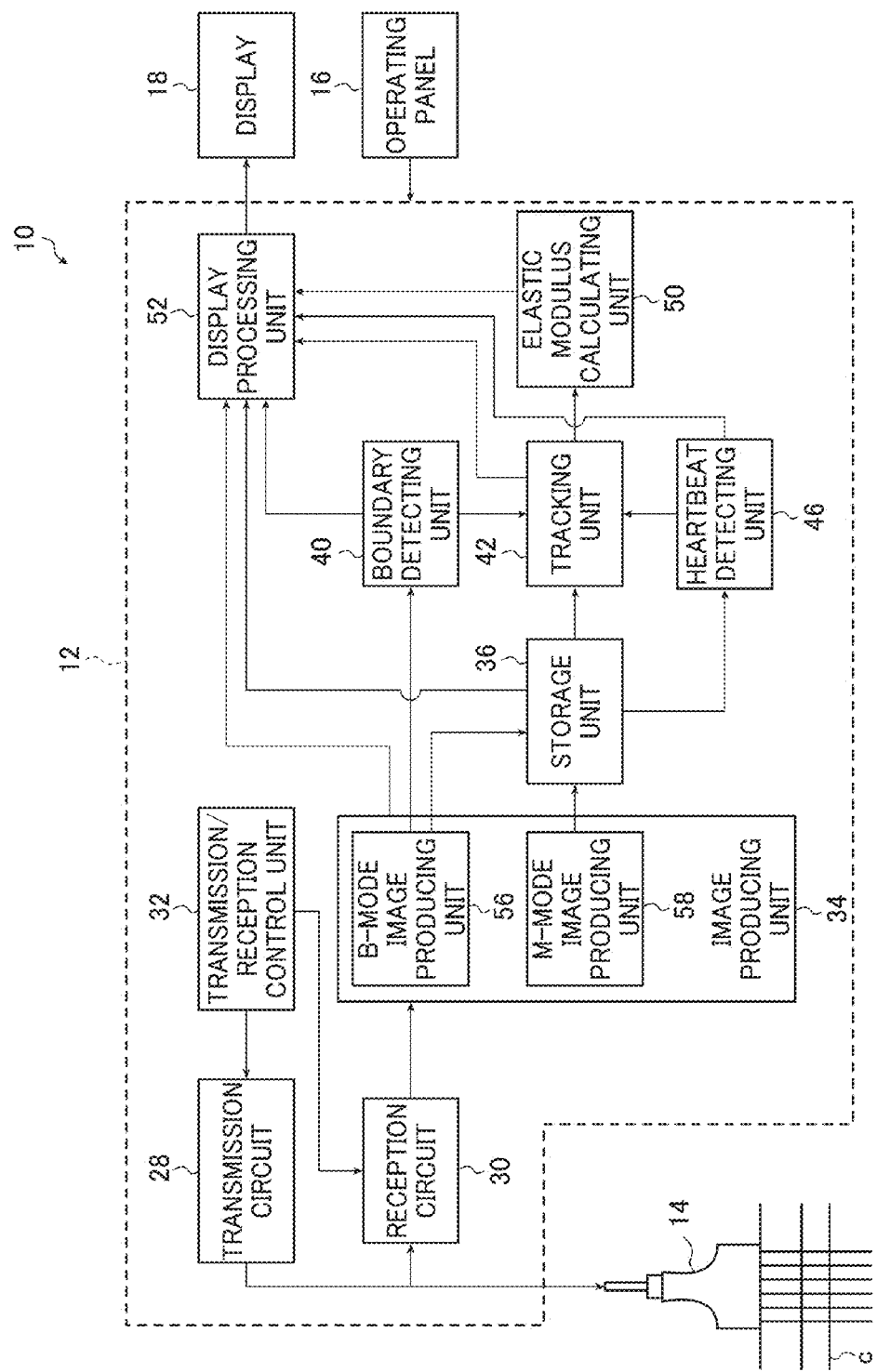
FIG. 2 is a block diagram conceptually showing the configuration of the ultrasound diagnostic apparatus shown in FIG. 1.
Figure 3:
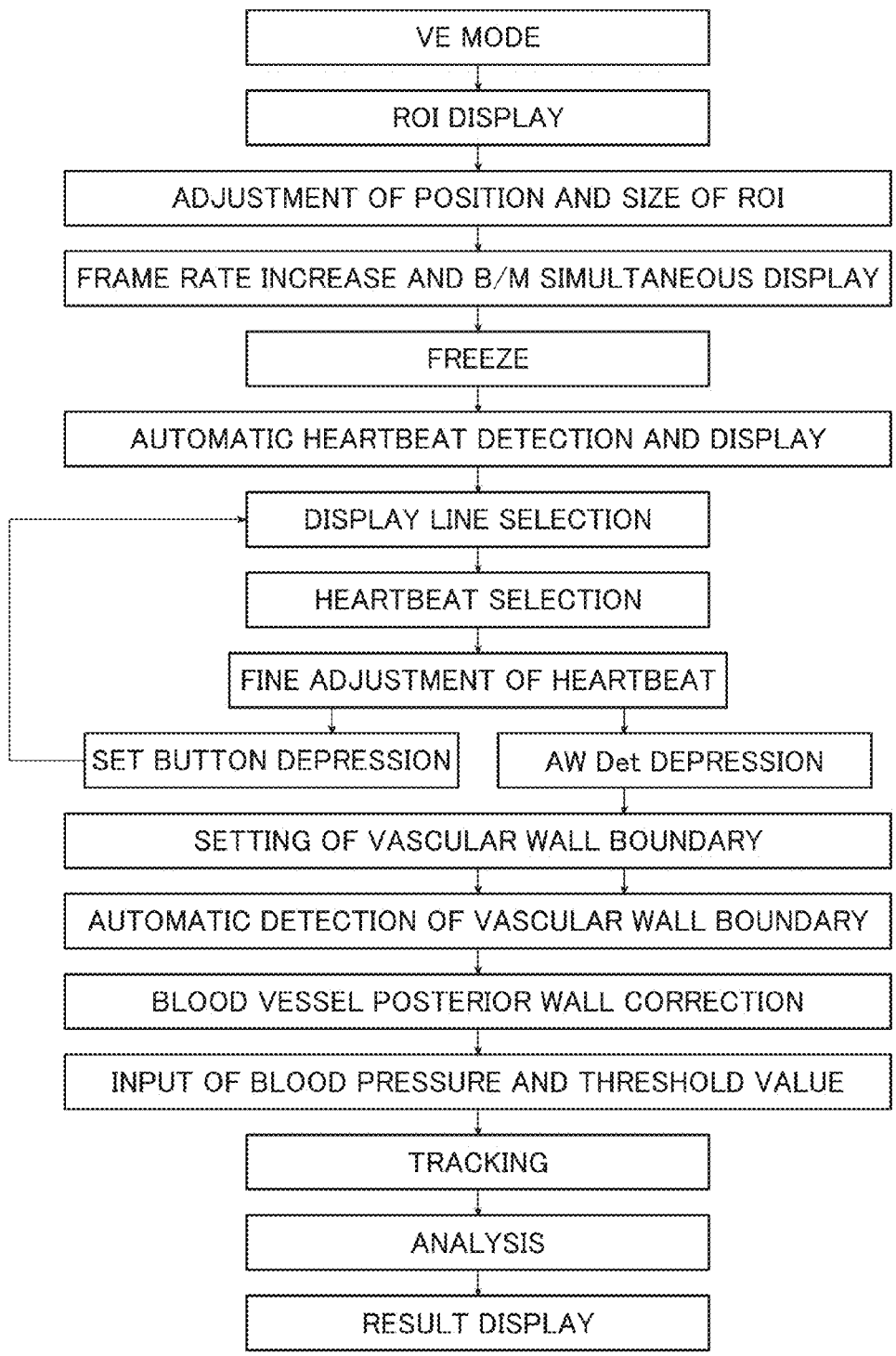
FIG. 3 is a flowchart for explaining an example of elasticity measurement of a vascular wall in the ultrasound diagnostic apparatus shown in FIG. 1.

FIG. 2 is a block diagram conceptually showing the configuration of the ultrasound diagnostic apparatus 10.

As shown in FIG. 2, the diagnostic apparatus body 12 has the transmission circuit 28, the reception circuit 30, the transmission/reception control unit 32, an image producing unit 34, a storage unit 36, a boundary detecting unit 40, a tracking unit 42, a heartbeat detecting unit 46, an elastic modulus calculating unit 50, and a display processing unit 52.

The image producing unit 34 has a B-mode image producing unit 56 and an M-mode image producing unit 58.

The above-mentioned probe 14 is connected to the transmission circuit 28 and the reception circuit 30. The transmission/reception control unit 32 is connected to the transmission circuit 28 and the reception circuit 30. The reception circuit 30 is connected to the image producing unit 34.

The image producing unit 34 is connected to the display processing unit 52. The B-mode image producing unit 56 and the M-mode image producing unit 58 of the image producing unit 34 are connected to the storage unit 36. The B-mode image producing unit 58 is also connected to the boundary detecting unit 40.

The storage unit 36 is connected to the tracking unit 42, the heartbeat detecting unit 46, and the display processing unit 52. The heartbeat detecting unit 46 and the boundary detecting unit 40 are connected to the tracking unit 42 and the display processing unit 52. The tracking unit 42 is connected to the display processing unit 52 and the elastic modulus calculating unit 50. The elastic modulus calculating unit 50 is connected to the display processing unit 52.

The transmission/reception control unit 32 sequentially sets a transmission direction of an ultrasonic beam and a reception direction of an ultrasonic echo of the probe 14 through the transmission circuit 28 and the reception circuit 30.

The transmission/reception control unit 32 also has a transmission control function of selecting a transmission delay pattern in accordance with the set transmission direction and a reception control function of selecting a reception delay pattern in accordance with the set reception direction.

The transmission delay pattern is a pattern of a delay time which is given to a driving signal for each of the ultrasound transducers so as to produce an ultrasonic beam in a desired direction by using ultrasonic waves transmitted from the ultrasound transducers of the probe 14. The reception delay pattern is a pattern of a delay time which is given to a reception signal so as to extract an ultrasonic echo from a desired direction by using ultrasonic waves received by the ultrasound transducers.

A plurality of transmission delay patterns and a plurality of reception delay patterns are stored in an internal memory (not illustrated), and are appropriately selected and used depending on the situation.

The transmission circuit 28 has a plurality of channels and produces a plurality of driving signals to be separately applied to each of the ultrasound transducers of the probe 14. At this time, a delay time can be given to each of the driving signals based on the transmission delay pattern selected by the transmission/reception control unit 32.

The transmission circuit 28 may adjust delay amounts of the driving signals and then supply the adjusted driving signals to the respective ultrasound transducers of the probe 14 so that the ultrasonic waves transmitted from the ultrasound transducers form an ultrasonic beam, or may supply to the probe 14 the driving signals configured so that ultrasonic waves transmitted from the ultrasound transducers at a time reach the entire imaging region of the subject.

The reception circuit 30 which has a plurality of channels similarly to the transmission circuit 28 amplifies a plurality of analog signals received through the ultrasound transducers and converts the amplified analog signals to digital reception signals.

Furthermore, a reception focusing process is performed by giving the delay time to each of the reception signals based on the reception delay pattern selected by the transmission/reception control unit 32 and adding those reception signals. With this reception focusing process, the ultrasonic echo is well focused so as to produce a sound ray signal (sound ray data).

The produced sound ray data is supplied to the image producing unit 34.

The image producing unit 34 performs a preprocess such as Log (logarithmic) compression and gain adjustment on the supplied sound ray data to produce image data of an ultrasound image, converts (raster-converts) the image data to image data according to a normal television signal scan system, performs necessary image processes such as a gradation process on the image data, and outputs the image data to the display processing unit 52.

The image producing unit 34 has the B-mode image producing unit 56 which produces a B-mode image, and the M-mode image producing unit 58 which produces an M-mode image. The B-mode image and the M-mode image may be produced by a known method.

The display processing unit 52 produces display data for use in display on the display 18 in accordance with image data of the ultrasound image supplied from the image producing unit 34, image data of the ultrasound image read out from the storage unit 36, the operation (input instruction) made through the operating panel 16, measurement results (analysis results) of a vascular wall elastic modulus described below, and the like, and displays them on the display 18.

In the ultrasound diagnostic apparatus 10 of the illustrated example, the storage unit 36, the boundary detecting unit 40, the tracking unit 42, the heartbeat detecting unit 46, and the elastic modulus calculating unit 50 of the diagnostic apparatus body 12 are mainly used in the VE mode in which an elastic modulus of a vascular wall is measured.

Hereinafter, the respective units such as the storage unit 36 and the boundary detecting unit 40, and the ultrasound diagnostic apparatus 10 of the invention will be explained in further detail by explaining the function of the ultrasound diagnostic apparatus 10 in the VE mode with reference to a flowchart of FIG. 3 and FIGS. 5 to 12.

In the following explanation, with regard to the display on the display 18, the display processing unit 52 performs necessary processes such as production of lines, even though not particularly described.

When an ultrasound diagnosis by the ultrasound diagnostic apparatus 10 is started, under the control by the transmission/reception control unit 32, the transmission circuit 28 causes the ultrasound transducers of the probe 14 to transmit ultrasonic waves, and the reception circuit 30 processes a reception signal output from the probe 14 to produce a sound ray signal and outputs the sound ray signal to the image producing unit 34.

Figure 4:
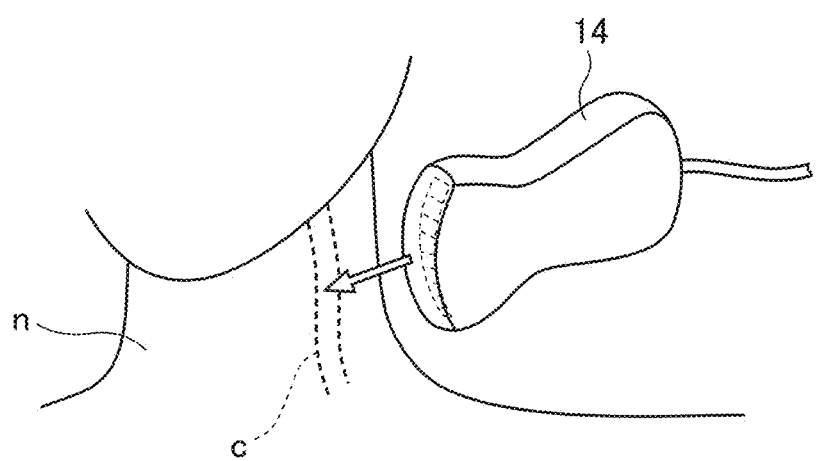
FIG. 4 is a conceptual diagram for explaining an ultrasound diagnosis for elasticity measurement of a vascular wall.

As an example, assuming that the B mode is selected, a carotid artery c of the subject is taken as a measurement target, and the probe 14 is brought into contact with the neck n as conceptually shown in FIG. 4, a B-mode image produced by the image producing unit 34 (B-mode image producing unit 56) is processed by the display processing unit 52 and displayed on the display 18.

Figure 5A:
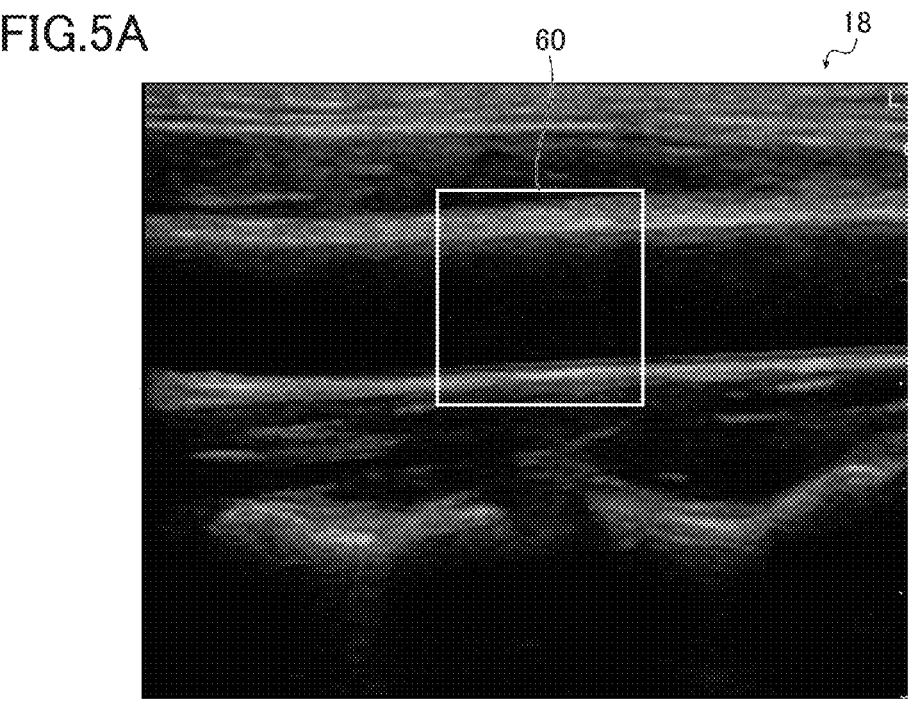
FIGS. 5A and 5B are conceptual diagrams each showing an example of image display in the ultrasound diagnostic apparatus shown in FIG. 1.

When the target carotid artery c can be appropriately observed and the VE mode is selected with the mode selecting means of the operating panel 16 (in the following description, "of the operating panel 16" is omitted), the display processing unit 52 displays an ROI 60 representing a region of interest in the B-mode image as conceptually shown in FIG. 5A.

Under this condition, the position of the ROI 60 in the B-mode image can be moved by operation of the trackball. When the set button is pressed, the position of the ROI 60 is fixed and the size of the ROI 60 can be changed by operation of the trackball.

Each time the set button is pressed, the implementable operation is alternately switched between the position change of the ROI 60 and the size adjustment of the ROI 60.

When the zoom button is pressed (depressed) under this condition, it is determined that the adjustment of the position and the size of the ROI 60 has finished and the setting of the ROI 60 has been instructed. In response, the transmission/reception control unit 32 increases the frame rate to be higher than that of before the setting of the ROI 60 is instructed (for example, to be equal to or higher than 200 Hz or at least five times the value of before the ROI setting is instructed). In addition, in response to the depression of the zoom button, the M-mode image producing unit 58 starts to produce an M-mode image of the ROI 60 and, as shown in FIG. 5B, a B-mode image 64 where the portion of the ROI 60 is enlarged and an M-mode image 65 of the ROI 60 (at a selection line 62 thereof) are displayed simultaneously.

The simultaneous display (dual mode display) of the B-mode image 64 and the M-mode image 65 may be performed in the same manner as the so-called B/M-mode display in a known ultrasound diagnostic apparatus.

Figure 5B:
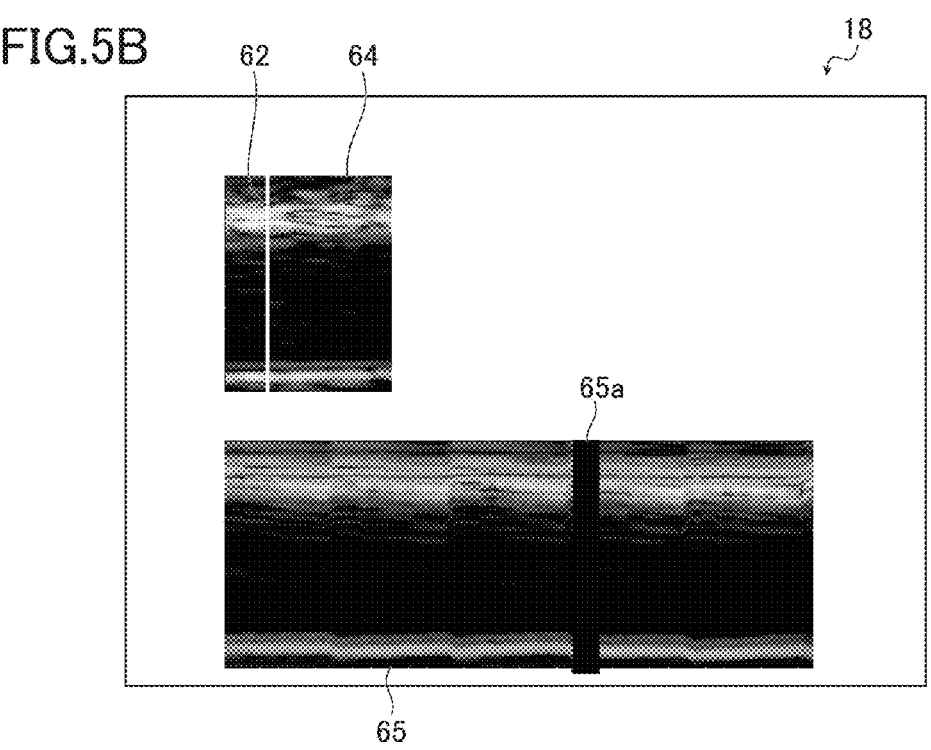

In FIG. 5B, the upper side is the B-mode image 64, and the lower side is the M-mode image 65.

In the B-mode image 64, the horizontal direction in the drawing is the azimuth direction (the direction along the array of the ultrasound transducers (in the case of the two-dimensional array, the longitudinal direction)), the vertical direction is the depth direction (the transmission/reception direction of ultrasonic waves), and the upper side is the side on which the depth is shallower (the probe 14 side).

A selection line 62 extending in the depth direction and used to select an M-mode image display position (a display line of the M-mode image) in the azimuth direction in the B-mode image is displayed in the B-mode image. The selection line 62 is movable in the azimuth direction (left-right direction) by the trackball.

In the M-mode image 65, the horizontal direction represents the time axis, the time flows from left to right, and the frame on the left side of a gap 65a is a current frame (that is, the frame on the right side of the gap 65a is a past frame). Similarly to the B-mode image 64, the vertical direction is the depth direction and the upper side is the side on which the depth is shallower.

In FIG. 5B, the M-mode image 65 displayed on the display 18 is the M-mode image 65 of the position of the selection line 62 whose position is set in advance.

The M-mode image producing unit 58 produces not only an M-mode image of a predetermined position (a predetermined position set in advance or a selected position) in the azimuth direction or a selected position in the azimuth direction but also M-mode images over the entire region along the azimuth direction in the B-mode image 64.

The B-mode image (B-mode image data) of the ROI 60 produced by the B-mode image producing unit 56 and the M-mode image (M-mode image data) produced by the M-mode image producing unit 58 are both stored in the storage unit 36.

While the amount of an image stored in the storage unit 36 in terms of time is not particularly limited, a time length corresponding to two or more heartbeats of common level is preferred. Accordingly, the storage unit 36 preferably stores the latest B-mode image and M-mode image each corresponding to three seconds or longer.

As described above, the selection line 62 is movable in the azimuth direction by the trackball.

The position of the selection line 62 and the M-mode image 65 are linked with each other. Specifically, when the selection line 62 is moved in the left-right direction by the trackball, the display processing unit 52 displays an M-mode image 65 of the position of the moved selection line 62 on the display 18.

Upon determining that an appropriate image has been obtained, the operator presses the freeze button.

When the freeze button is pressed, the display processing unit 52 reads out necessary image data from the storage unit 36, and as shown in FIG. 6A, displays on the display 18 the M-mode image 65 of the position of the selection line 62 after rearranging the image so that the time at which the freeze button is pressed is located at the rightmost position (as the latest time), as well as displaying a still image of the B-mode image 64. Simultaneously, the selection line 62 changes to a broken line and becomes immovable (becomes inactive).

As shown in FIG. 6B, an "AW Det" button used for instructing the setting of a boundary of a vascular wall to be described below, an "Elasticity Ana" button used for instructing the start of analysis of a vascular wall elastic modulus, a "Ps" button and a "Pd" button used for inputting a blood pressure of the subject, and a "Quality Factor Threshold" button used for inputting a reliability threshold value are displayed in the touch panel 16a of the operating panel 16. Note that, at this time, the "Elasticity Ana" button is in the non-selectable state.

When the freeze button is pressed, the heartbeat detecting unit 46 detects heartbeats (performs automatic detection of heartbeats) for all the M-mode images stored in the storage unit 36. The detection result of heartbeats is sent to the storage unit 36 to be added to the corresponding M-mode images as information.

The detection result of heartbeats is also sent to the display processing unit 52 so that the detection result of heartbeats is displayed in the M-mode image 65 currently displayed.

While a method of detecting heartbeats is not particularly limited, heartbeats may be detected by analyzing an M-mode image and using the moving velocity in the depth direction of a white line (bright line) extending in the horizontal direction (the time point at which the velocity starts to increase), the pulsation of the motion of the white line in the depth direction. Alternatively, an electrocardiograph (electrocardiogram) may be used to detect heartbeats.

As shown in FIG. 6A, the display processing unit 52 displays the detection result of heartbeats in the M-mode image 65 with triangular marks and straight lines. In the illustrated example, the time point at which the latest heartbeat starts is indicated by a solid line, the time point at which the same heartbeat ends by a thin line, and positions related to other heartbeats by broken lines. Those lines may be distinguished by changing the line color instead of or in addition to the line type.

When there is a heartbeat which failed to be detected, the heartbeat is displayed at an appropriate position in accordance with intervals of heartbeats around the heartbeat in question, or the like.

The B-mode image 64 when the freeze button is pressed is a B-mode image at the time when the latest heartbeat starts, the time being indicated by a solid line in the M-mode image 65.

When the lines of heartbeats are displayed in the M-mode image 65, the selection line 62 in the B-mode image changes to a solid line and becomes movable in the left-right direction with the use of the trackball. That is, the selection line 62 becomes active. Whether or not the line is active may be distinguished by changing the line color instead of or in addition to the line type in a similar manner to the above.

Under this condition, when the selection line 62 is moved in the left-right direction by the trackball, the display processing unit 52 reads out an M-mode image corresponding to the position of the selection line 62 from the storage unit 36, and displays the image along with the detection result of heartbeats on the display 18. Specifically, even after freeze, a display position (display line) of the M-mode image 65 in the B-mode image 64 can be selected from the entire region along the azimuth direction in the B-mode image 64 by moving the selection line 62 by the trackball.

Therefore, according to the invention, the M-mode image 65 of an arbitrary position in the azimuth direction in the set RCI 60 is displayed, so that the M-mode image 65 and images corresponding to respective heartbeats in the M-mode image 65 can be observed and checked.

Figure 7A:
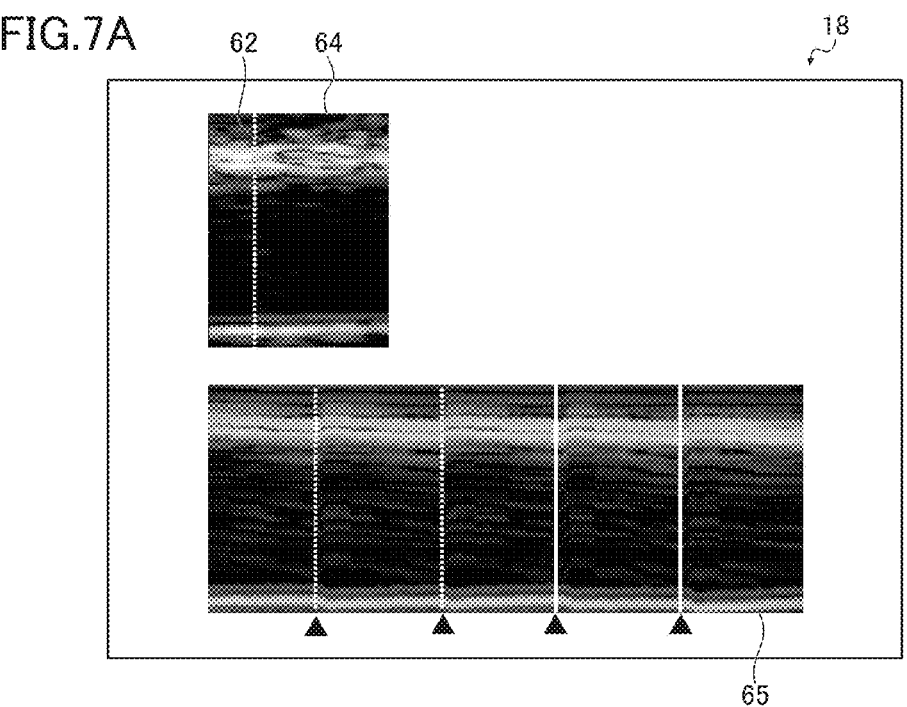
FIGS. 7A to 7C are conceptual diagrams each showing an example of image display in the ultrasound diagnostic apparatus shown in FIG. 1.

When the set button is pressed under the condition where the selection line 62 in the B-mode image 64 is movable, it is determined that the selection of the display position (display line) of the M-mode image 65 has finished and, as shown in FIG. 7A, the selection line 62 in the B-mode image 64 changes to a broken line and the movement by the trackball becomes impossible. Simultaneously, lines indicating the latest heartbeat both change to solid lines in the M-mode image 65.

When the lines indicating the latest heartbeat both change to solid lines in the M-mode image 65, the selection of a heartbeat with the use of the trackball becomes available.

Figure 7B:
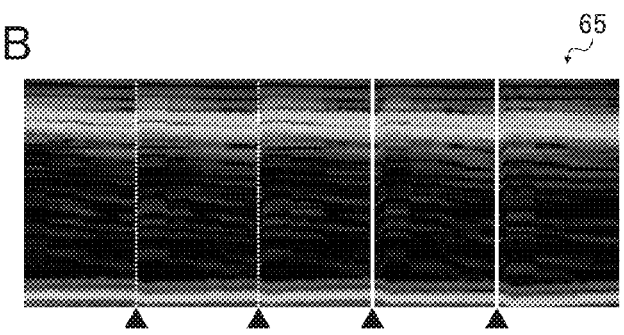
Figure 7C:
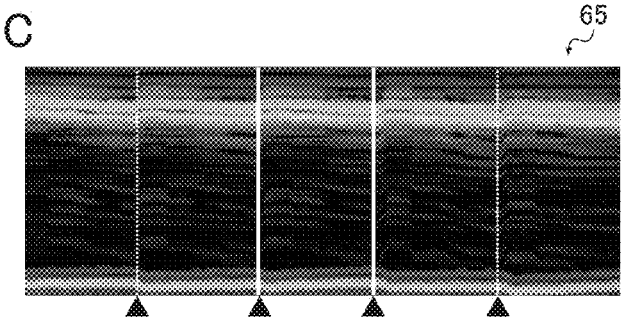

As an example, when the set button is pressed, as shown in FIGS. 7A and 7B, the lines indicating the latest heartbeat change to solid lines, i.e., are selected. Under this condition, for example, when the trackball is rotated left, as shown in FIG. 7C, a line corresponding to the end of the latest heartbeat changes to a broken line, and lines corresponding to the second latest heartbeat change to solid lines, so that this heartbeat is selected. When the trackball is further rotated left, the lines corresponding to the second latest heartbeat change to broken lines, and lines corresponding to the third latest heartbeat change to solid lines, so that this heartbeat is selected.

When the trackball is rotated right, in the same manner, lines corresponding to later heartbeats are sequentially selected.

Furthermore, in response to the selection of a heartbeat, the display processing unit 52 reads out from the storage unit 36 the B-mode image of the start position of the selected heartbeat, that is, the B-mode image which is captured at the time (time phase) corresponding to the start position of the selected heartbeat, and changes the B-mode image 64 displayed on the display 18 to this B-mode image.

When the set button is pressed under the condition where the heartbeat selection is available, it is determined that the heartbeat selection has finished, the selected heartbeat is confirmed, and fine adjustment of the selected heartbeat becomes performable.

When the heartbeat in the M-mode image 65 displayed on the display 18 is selected and confirmed, the same heartbeat is selected in all the M-mode images stored in the storage unit 36 (that is, M-mode images over the entire region along the azimuth direction of the B-mode image 64).

Figure 8A:
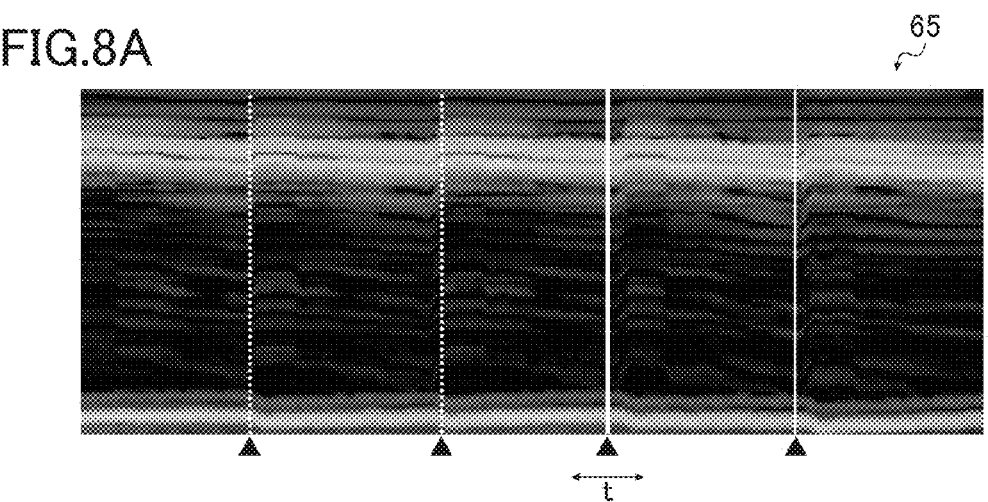
FIGS. 8A and 8B are conceptual diagrams each showing an example of image display in the ultrasound diagnostic apparatus shown in FIG. 1.

As an example, in the case where the latest heartbeat is selected, when the set button is pressed, as shown in FIG. 8A, first, the line corresponding to the end of the selected heartbeat changes to a thin line, and the position (time) of a line corresponding to the start of the selected heartbeat becomes movable in the left-right direction (time direction) with the use of the trackball as indicated by an arrow t, so that fine adjustment of the start position of the heartbeat can be performed.

Figure 8B:
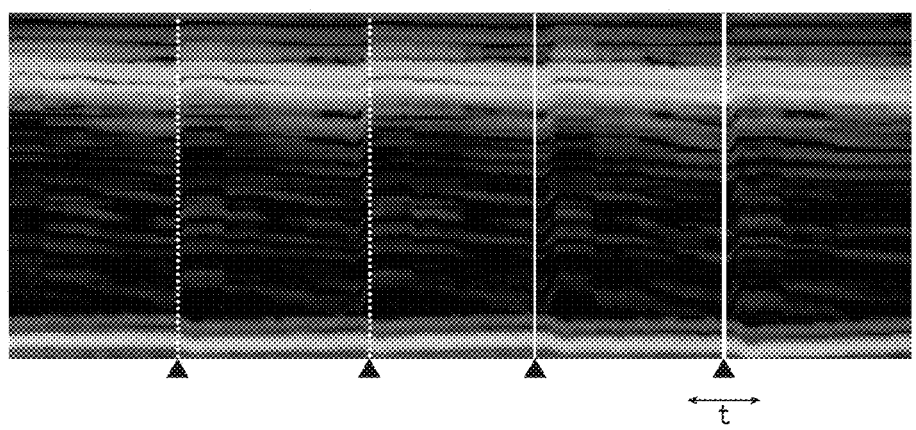

After the start position of the heartbeat is adjusted by the trackball as needed, when the set button is pressed again, as shown in FIG. 8B, the line corresponding to the end of the selected heartbeat changes to a normal solid line whilst the line corresponding to the start of the selected heartbeat changes to a thin line, and the position of the line corresponding to the end of the selected heartbeat becomes movable in the left-right direction with the use of the trackball as indicated by an arrow t, so that fine adjustment of the end position of the heartbeat can be performed.

While the result of fine adjustment of the heartbeat may be reflected only in the M-mode image 65 subjected to the fine adjustment, the result is preferably reflected also in all the M-mode images stored in the storage unit 36.

In the case where the start position of the heartbeat is adjusted, the display processing unit 52 reads out the B-mode image of the adjusted heartbeat start position from the storage unit 36, and the B-mode image 64 displayed on the display 18 is changed to this image.

The results of the heartbeat selection and possible fine adjustment are supplied also to the tracking unit 42.

When the set button is pressed under the condition where the position corresponding to the end of the selected heartbeat is adjustable, the state of the selection line 62 in the B-mode image 64 shown in FIG. 6 mentioned above returns to be movable. That is, the state returns to the condition where the display line of the M-mode image 65 in the B-mode image 64 is selectable.

Specifically, in the ultrasound diagnostic apparatus 10 of the illustrated example, the processes of "display line selection"→"heartbeat selection"→"heartbeat fine adjustment" can be repeatedly performed. In other words, the processes of "display line selection"→"heartbeat selection"→"heartbeat fine adjustment" can be performed in a looped manner.

Accordingly, it becomes possible to select the heartbeat optimal for analysis for the measurement of vascular wall elasticity to be described below from all the stored M-mode images in a further preferred manner.

Figure 9:
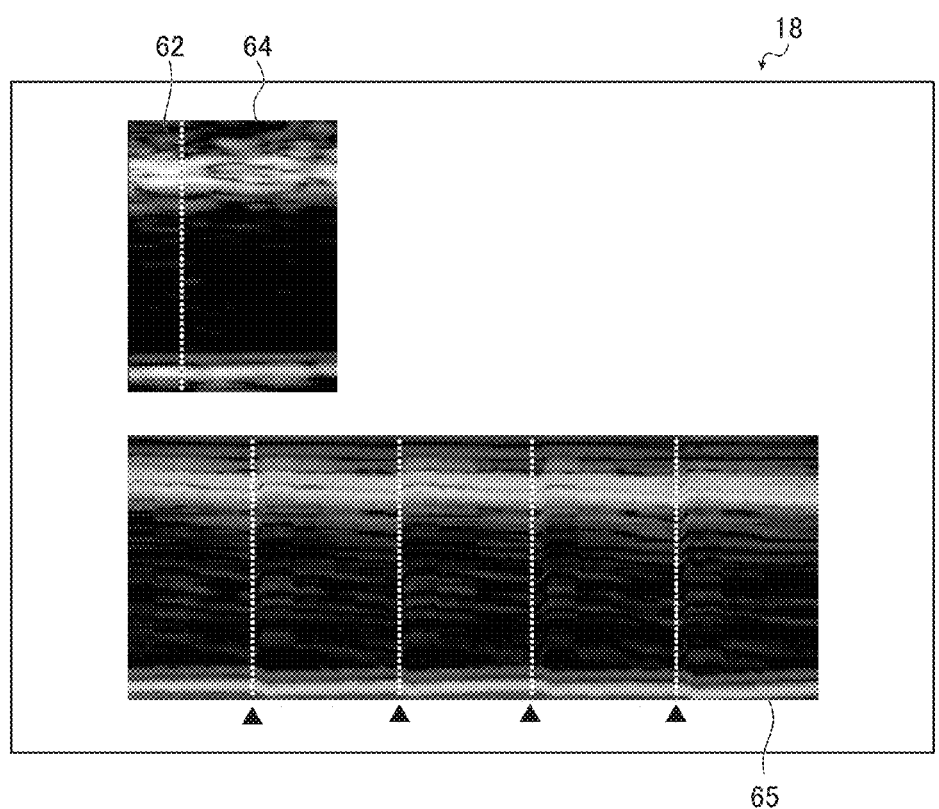
FIG. 9 is a conceptual diagram showing an example of image display in the ultrasound diagnostic apparatus shown in FIG. 1.

When not the set button but the "AW Det" button of the touch panel is pressed under the condition where the position corresponding to the end of the selected heartbeat is adjustable, as shown in FIG. 9, the selection line 62 in the B-mode image 64 and the lines representing the heartbeats in the M-mode image 65 all become broken lines and inoperable, and a vascular wall detection mode is established.

When the vascular wall detection mode is established, as shown in FIG. 10A, a line 68 corresponding to the adventitia-media boundary of the blood vessel anterior wall is displayed in the B-mode image 64.

The line 68 is movable parallel in the up-and-down direction (depth direction) by the trackball. As shown in FIG. 10B, when the line 68 is moved by the trackball to the position of the adventitia-media boundary of the blood vessel anterior wall, the set button is pressed.

When the set button is pressed, as shown in FIG. 10C, the line 68 corresponding to the adventitia-media boundary of the blood vessel anterior wall changes to a broken line in the B-mode image 64 and is thus confirmed, and a line 70 corresponding to the intima-lumen boundary of the blood vessel anterior wall is displayed.

Similarly, the line 70 is also movable in the up-and-down direction by the trackball, and when the line 70 is moved to the position of the intima-lumen boundary of the blood vessel anterior wall, the set button is pressed.

When the set button is pressed with the line 70 being movable, as shown in FIG. 10D, the line 70 corresponding to the intima-lumen boundary of the blood vessel anterior wall changes to a broken line in the B-mode image 64 and is thus confirmed, and a line 72 corresponding to the intima-lumen boundary of the blood vessel posterior wall is displayed. Similarly, when the line 72 is moved by the trackball to the position of the intima-lumen boundary of the blood vessel posterior wall, the set button is pressed.

Then, when the set button is pressed with the line 72 being movable, as shown in FIG. 10E, the line 72 corresponding to the intima-lumen boundary of the blood vessel posterior wall changes to a broken line in the B-mode image 64 and is thus confirmed, and a line 74 corresponding to the adventitia-media boundary of the blood vessel posterior wall is displayed. Similarly, when the line 74 is moved by the trackball to the position of the adventitia-media boundary of the blood vessel posterior wall, the set button is pressed.

Information on each boundary of the vascular walls is supplied to the boundary detecting unit 40.

When the set button is pressed with the line 74 being movable, the setting of the lines corresponding to all the boundaries finishes, and the boundary detecting unit 40 performs automatic detection of the intima-lumen boundary and the adventitia-media boundary of the blood vessel posterior wall using the set line 72 for the intima-lumen boundary and the set line 74 for the adventitia-media boundary. The results of the automatic detection of the two boundaries are sent to the display processing unit 52 and the tracking unit 42, and as shown in FIG. 10F, the detection results are displayed.

A method of automatic detection of those boundaries is not particularly limited and several methods may be used. As an example, a method in which the B-mode image 64 is analyzed and continuous high-intensity portions on the line 72 and the line 74 are traced to thereby detect the intima-lumen boundary and the adventitia-media boundary, is mentioned.

When the automatic detection of the intima-lumen boundary and the adventitia-media boundary of the blood vessel posterior wall by the boundary detecting unit 40 finishes, as shown in FIG. 10F, a cursor 78 is displayed in the B-mode image 64 (this cursor 78 is not displayed before the automatic detection of the blood vessel posterior wall finishes).

The cursor 78 is movable by the trackball. When the cursor 78 is moved toward either one of the lines indicative of the automatically-detected intima-lumen boundary and adventitia-media boundary and the set button is pressed, the line closer to the cursor 78 changes to a solid line. The line having changed to a solid line is correctable.

As an example, as shown in FIG. 10G, it is assumed that the line 74 indicative of the adventitia-media boundary is selected and changes to a solid line. When the cursor 78 is moved along the line 74 by the trackball and the set button is again pressed, the line 74 of the region traced by the cursor is again detected by the boundary detecting unit 40 and rewritten, and the result is sent to the tracking unit 42.

Figure 11A:
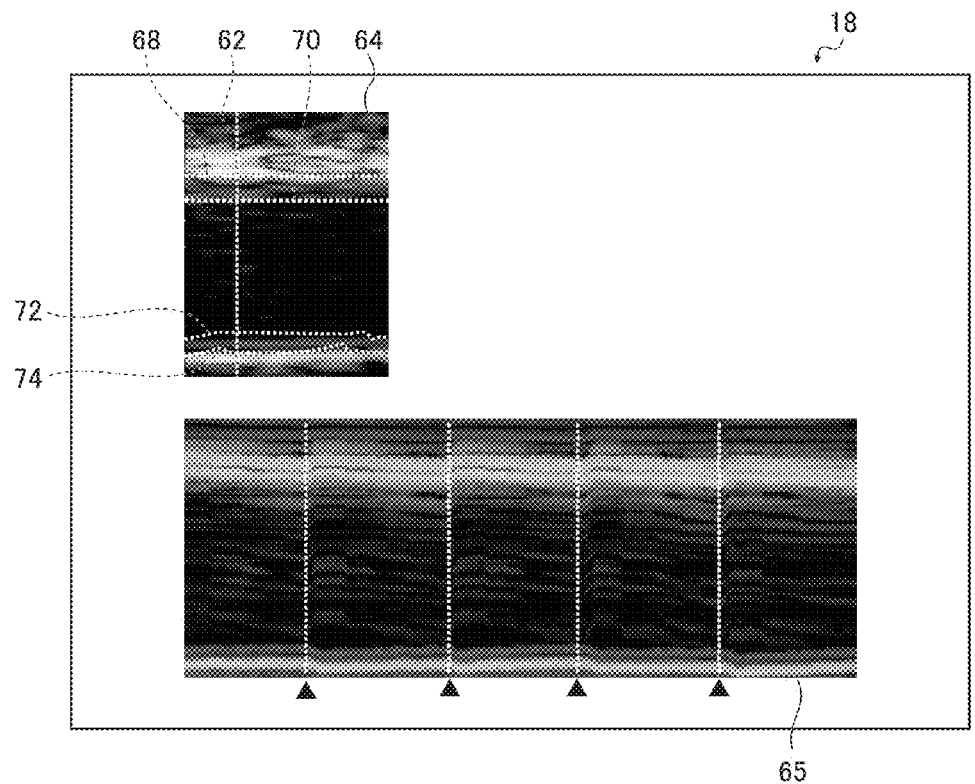
FIGS. 11A and 11B are conceptual diagrams each showing an example of image display in the ultrasound diagnostic apparatus shown in FIG. 1.
Figure 11B:
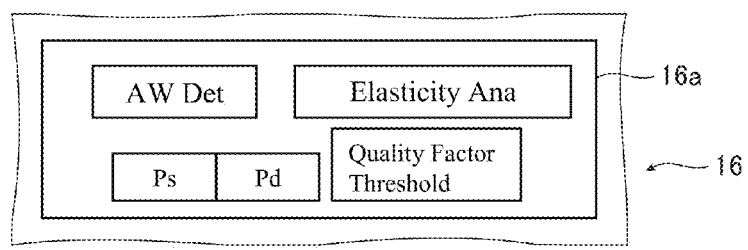

When the automatic detection of the intima-lumen boundary and the adventitia-media boundary of the posterior wall finishes and the blood vessel posterior wall is corrected as needed, as shown in FIG. 11A, all the lines become broken lines and as shown in FIG. 11B, the "Elasticity Ana" button of the touch panel 16a becomes selectable.

After the "Elasticity Ana" button becomes selectable, the systolic blood pressure of the subject is input using the "Ps" button whilst the end-diastolic blood pressure of the subject is input using the "Pd" button, and the reliability threshold value is input using the "Quality Factor Threshold" button. Those numerical values may be input by a known method.

The input of the blood pressure of the subject and the reliability threshold value is not limited to the input after the detection of the vascular wall boundaries finishes, and may be carried out at any timing as long as it is before the analysis described below starts (before depression of the "Elasticity Ana" button described below).

In the ultrasound diagnostic apparatus 10, subject information is normally acquired and input before a diagnosis is performed, and hence, when the subject information contains information on the blood pressure, this information may be used.

When the blood pressure of the subject and the reliability threshold value are input and the "Elasticity Ana" button is pressed, analysis of the B-mode image starts and the elastic modulus of the vascular wall is calculated.

When the "Elasticity Ana" button is pressed, first, the tracking unit 42 performs tracking of motions of the blood vessel anterior wall (adventitia-media boundary and intima-lumen boundary) and the blood vessel posterior wall (intima-lumen boundary and adventitia-media boundary) in the selected heartbeat in the M-mode image 65. That is, the blood vessel anterior wall and posterior wall are tracked.

The tracking of the vascular wall in the M-mode image 65 is performed with the adventitia-media boundary of the blood vessel anterior wall, the intima-lumen boundary of the blood vessel anterior wall, the intima-lumen boundary of the blood vessel posterior wall, and the adventitia-media boundary of the blood vessel posterior wall as previously detected (set) in the B-mode image 64 being defined as positional starting points (starting points in the depth direction).

In the tracking of the vascular wall in the M-mode image 65, a temporal starting point (a starting point on the time axis of the M-mode image) is the time phase of the B-mode image 64, that is, the time at which the B-mode image 64 is captured. Specifically, in the illustrated example, the start position of the heartbeat which is selected and adjusted in position as needed is to be the temporal starting point for the tracking of the vascular wall.

In the ultrasound diagnostic apparatus 10, as a preferred embodiment, in addition to the detected (set) boundaries of the vascular walls, one or more measurement points may be set in the depth direction in the blood vessel posterior wall. In the case where one or more measurement points are thus set in the blood vessel posterior wall, the tracking of the vascular wall is performed at each measurement point.

The measurement point in the vascular wall may be set in advance, may be automatically set based on a specific algorithm, may be set by the operator of the ultrasound diagnostic apparatus 10 while viewing the image, or may be set through a combination of those methods.

A method of tracking the vascular wall in the M-mode image 65 is not particularly limited, and exemplary methods include a method which uses continuity of images (luminance) from the starting point of the tracking, a pattern matching method, a zero crossing method, a tissue Doppler method, and phase difference tracking, any of which may be used.

The results of tracking of the vascular walls in the M-mode image by the tracking unit 42 are supplied to the elastic modulus calculating unit 50 and the display processing unit 52.

The elastic modulus calculating unit 50 first produces a change waveform of the thickness of the vascular wall (intima-media) and a change waveform of the blood vessel diameter (inner diameter) based on the tracking results of the vascular wall. When one or more measurement points are set in the vascular wall as described above, a change waveform of the vascular wall is produced for each portion between measurement points.

The change waveform of the thickness of the vascular wall and the change waveform of the blood vessel diameter are sent to the display processing unit 52.

The elastic modulus calculating unit 50 calculates the strain of the blood vessel in the radial direction using Equation (1).

$$\varepsilon_i = \Delta h_i / h_{di} \tag{1}$$

In Equation (1), $\varepsilon_i$ denotes the strain of the blood vessel in the radial direction between measurement points, $\Delta h_i$ denotes the maximum value of a change in thickness of the vascular wall between the measurement points in systole in which the vascular wall is thinnest during one heartbeat, and $h_{di}$ denotes the thickness between the measurement points in end diastole in which the vascular wall is thickest.

Further, the elastic modulus calculating unit 50 calculates an elastic modulus $E_{\theta i}$ of the vascular wall in the circumferential direction by Equation (2) using the maximum value and the minimum value of the blood pressure input in advance.

$$E_{\theta i} = \frac{1}{2} * [1 + (r_d / h_d)] * [\Delta p / (\Delta h_i / h_{di})] \tag{2}$$

Alternatively, an elastic modulus $E_{ri}$ of the vascular wall in the radial direction may be calculated by Equation (3).

$$E_{ri} = \Delta p / (\Delta h_i / h_{di}) \tag{3}$$

In Equations (2) and (3), $\Delta h_i$ and $h_{di}$ are the same as above, $\Delta p$ denotes a difference in blood pressure between systole and end diastole, $r_d$ denotes a radius of the vascular lumen in end diastole, and $h_d$ denotes the thickness of the vascular wall in end diastole.

After calculating the elastic modulus, the elastic modulus calculating unit 50 calculates the reliability of the elastic modulus.

A method of calculating the reliability of the elastic modulus is not particularly limited, and various known methods may be used. As an example, mentioned is a method in which waveforms of blood vessel diameter changes due to heartbeats of many people such as 1000 persons are produced; a model waveform of the blood vessel diameter change is produced based on those many waveforms; and the reliability of the calculated elastic modulus is calculated using a shift amount from the model waveform.

As described above, when a heartbeat is selected and confirmed in the M-mode image 65 displayed on the display 18, the same heartbeat is selected in all the M-mode images stored in the storage unit 36.

Accordingly, the processes such as the tracking of the vascular wall, the production of the change waveforms of the thickness of the vascular wall and the blood vessel diameter, the calculation of the strain of the vascular wall, and the calculation of the elastic modulus of the vascular wall and the reliability of the elastic modulus, are performed for the selected heartbeat not only in the M-mode image 65 displayed on the display 18 but also in all the M-mode images stored in the storage unit 36. Specifically, the processes such as the calculation of the elastic modulus of the vascular wall in the selected heartbeat are performed for the entire region along the azimuth direction of the B-mode image 64 displayed on the display 18 using corresponding M-mode images.

Results of those are added to the M-mode images stored in the storage unit 36 as information.

After the calculation over the entire region along the azimuth direction finishes, the elastic modulus calculating unit 50 calculates the average value ($E_{\theta Ave}$) of the elastic modulus of the vascular wall, the average value ($Str_{Ave}$) of the strain of the vascular wall, and the average value ($QF_{Ave}$) of the reliability of the elastic modulus.

When the calculation finishes, the results are displayed on the display 18.

Figure 12:
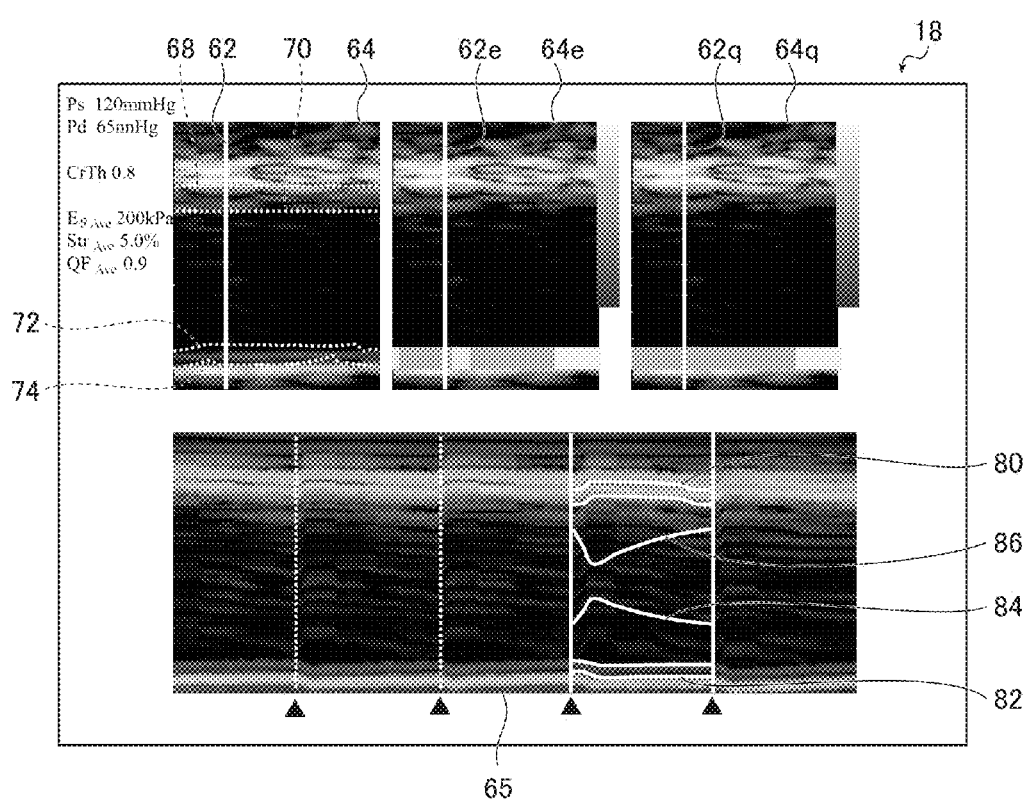
FIG. 12 is a conceptual diagram showing an example of image display in the ultrasound diagnostic apparatus shown in FIG. 1.

An example thereof is shown in FIG. 12. In the illustrated example, on the right side of the originally-displayed B-mode image 64 in the drawing, the elastic modulus of the blood vessel posterior wall shown in this B-mode image 64 is displayed in a B-mode image 64e. Further, on the right side in the drawing of the B-mode image 64e which displays the elastic modulus of the blood vessel posterior wall, the calculated reliability of the elastic modulus of the vascular wall is displayed in a B-mode image 64q in a similar manner.

On the left side of the B-mode image 64 in the drawing, the average value ($E_{\theta Ave}$) of the elastic modulus of the vascular wall, the average value ($Str_{Ave}$) of the strain of the vascular wall, and the average value ($QF_{Ave}$) of the reliability of the elastic modulus are displayed.

The elastic modulus of the vascular wall is displayed in a strip shape in the B-mode image 64e so as to overlap the blood vessel posterior wall automatically detected (and corrected as needed) in the B-mode image 64. On an upper right side of the B-mode image 64e, an index of the elastic modulus is displayed. In the illustrated example, the higher the image density is, the higher the elastic modulus is.

Specifically, in the B-mode image 64e, the density of the strip overlapping the blood vessel posterior wall represents the elastic modulus of the vascular wall at that position of the blood vessel.

Similarly, the reliability of the elastic modulus is displayed in a strip shape in the B-mode image 64q so as to overlap the blood vessel posterior wall automatically detected in the B-mode image 64. On an upper right side of the B-mode image 64q, an index of the reliability of the elastic modulus is displayed. In the illustrated example, the higher the image density is, the higher the reliability of the elastic modulus is.

Specifically, in the B-mode image 64q, the density of the strip overlapping the blood vessel posterior wall represents the reliability of the elastic modulus of the vascular wall at that position of the blood vessel.

The magnitude of the elastic modulus or the reliability of the elastic modulus may be expressed by changing the color of the image instead of or in addition to the density of the image.

In the display of the results shown in FIG. 12, the result at the position in the azimuth direction where the reliability is lower than the threshold value input in advance is automatically omitted.

At the position where the result is omitted, as indicated in the right corner portion of the result display of the elastic modulus in the B-mode image 64e and the right corner portion of the result display of the reliability in the B-mode image 64q, the display of the strip becomes pale.

In the M-mode image 65 on the lower side, a tracking result 80 of the blood vessel anterior wall and a tracking result 82 of the blood vessel posterior wall as well as a change waveform 84 of the blood vessel diameter and a change waveform 86 of the thickness of the vascular wall in the M-mode image, are displayed in the selected heartbeat.

As described above, when one or more measurement points are set in the vascular wall in the depth direction, the change waveform of the blood vessel thickness may be output for each portion between the measurement points.

When the measurement result of the elastic modulus of the vascular wall and the like are displayed on the display 18, the selection line 62 in the B-mode image 64 changes to a solid line and becomes movable in the azimuth direction by the trackball.

When the selection line 62 is moved in the B-mode image 64, the display processing unit 52 reads out an M-mode image corresponding to the position of the selection line 62 from the storage unit 36 and displays the M-mode image on the display 18. Specifically, when the selection line 62 is moved by the trackball, the M-mode image 65 is changed to an M-mode image of the position of the selection line 62, and the tracking result 80 of the blood vessel anterior wall and the tracking result 82 of the blood vessel posterior wall as well as the change waveform 84 of the blood vessel diameter and the change waveform 86 of the thickness of the vascular wall in the M-mode image 65 are changed to data at the position of the selection line 62 of the B-mode image 64.

Accordingly, it is possible to select a display line used for displaying the M-mode image 65 and the analysis result in the entire region along the azimuth direction of the B-mode image 64.

In synchronization with the movement of the selection line 62 in the B-mode image 64, a selection line 62e in the B-mode image 64e and a selection line 62q in the B-mode image 64q are also moved.

When, after the set button is pressed, the selection line 62e and the selection line 62q are moved by the trackball to select an arbitrary region along the azimuth direction in the B-mode image 64e and the B-mode image 64q, and thereafter, the set button is pressed again, the selected region is treated similarly to the above-mentioned region where the reliability is lower than the threshold value, so that data is deleted.

Specifically, when the tester views the result and finds a location where the waveform or the like seems strange, the corresponding data can be deleted, thereby making it possible to perform more accurate analysis.

In this operation of deleting data, the previous condition may be restored by depressing a Delete button or the like.

As described above, in order to perform accurate measurement when measuring an elastic modulus of a vascular wall by analyzing an M-mode image, it is important to select a heartbeat with which an image less affected by blurring due to hand movement or body movement, irregular heartbeats, speckles, or the like and thus suitable for analysis is reproduced.

However, in a conventional ultrasound diagnostic apparatus capable of performing the B/M mode display, only an M-mode image of a predetermined position in a B-mode image is displayed and hence, the displayed M-mode image does not necessarily include a suitable heartbeat which is not affected by blurring due to hand movement, speckles, or the like.

In contrast, in the ultrasound diagnostic apparatus of this invention, by having not only an M-mode image of a predetermined position in the azimuth direction in the B-mode image 64 but also M-mode images over the entire region along the azimuth direction in the B-mode image 64, and selecting a position of the selection line 62 (selecting the display line) in the B-mode image 64, it becomes possible to display an M-mode image 65 of an arbitrary position in the azimuth direction.

Therefore, according to the ultrasound diagnostic apparatus of this invention, from among M-mode images 65, the M-mode image of the heartbeat that is most suitable for analysis can be selected. In addition, heartbeats are automatically detected and the fine adjustment of automatically-detected heartbeats can be performed, which makes it possible to perform the analysis using a further suitable heartbeat, as well as improving the operability. Furthermore, the selection of a suitable heartbeat and other operations as described above can be carried out only by position selecting means and determining means such as the trackball and the set button.

In an M-mode image, a situation may arise in which the same heartbeat is suitable at one position in the azimuth direction and improper at another position. As to this point, according to the invention, since the same heartbeat can be checked at plural positions in the azimuth direction, a suitable heartbeat can be selected in a more favorable manner. In particular, since in response to the selection of a heartbeat in the displayed M-mode image 65, the condition where the corresponding heartbeat is in the selected state in all of the other M-mode images is established, the check of the same heartbeat at plural positions in the azimuth direction can be performed in a more favorable manner.

Further, since in response to the selection of a heartbeat in the displayed M-mode image 65, the corresponding heartbeat is selected in all the M-mode images, the measurement of a elastic modulus over the entire region along the azimuth direction in the B-mode image, and other operations, can also be accurately performed using a suitable heartbeat.

In the foregoing example, the B-mode image 64 is displayed on the upper side of the display 18 whilst the M-mode image 65 is displayed on the lower side, although this invention is not limited thereto.

Figure 13:
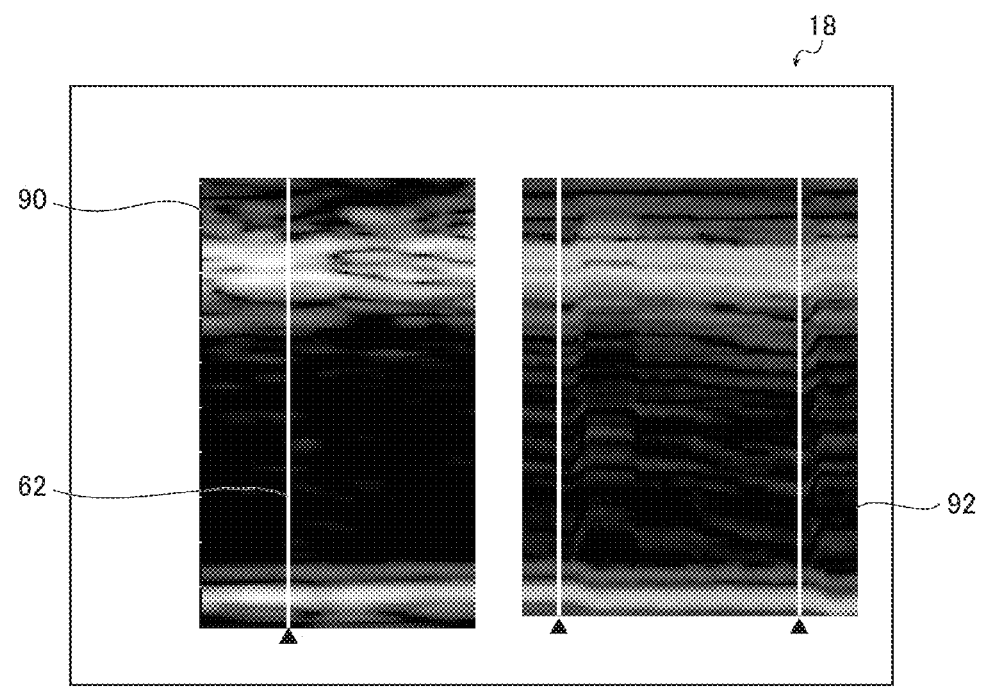
FIG. 13 is a conceptual diagram for explaining another example of image display in the ultrasound diagnostic apparatus shown in FIG. 1.

For instance, as shown in FIG. 13, a B-mode image 90 and an M-mode image 92 may be laterally arranged on the display 18. Alternatively, either a display style in which a B-mode image and an M-mode image are displayed on the upper side and the lower side, respectively, or a display style of the lateral arrangement shown in FIG. 13 may be selectable.

With the use of such a display method in which the B-mode image 90 and the M-mode image 92 are laterally arranged, the B-mode image and the M-mode image can be further enlarged, which makes it possible to further accurately perform, for example, setting of vascular wall boundaries.

However, in this display method of lateral arrangement, it is only one heartbeat or thereabout that can be displayed in the M-mode image 92.

Therefore, when employing the lateral arrangement display, it is preferred that the M-mode image 92 can be scrolled laterally (in a direction of the time course) so that a past heartbeat can be displayed, and that the display can be returned from a past heartbeat to a new heartbeat. While a scroll method is not particularly limited, as an example, one method can be achieved by, in the foregoing operation of selecting a heartbeat using the trackball, automatically displaying the selected heartbeat in the middle of the M-mode image.

While the ultrasound diagnostic apparatus of the invention has been described above in detail, the invention is by no means limited to the above examples, and various modifications and improvements may be made without departing from the scope and spirit of the invention.

What is claimed is:

1. An ultrasound diagnostic apparatus comprising:
    an ultrasound probe which has ultrasound transducers transmitting ultrasonic waves, receiving an ultrasonic echo reflected by a subject, and outputting a reception signal according to the received ultrasonic echo;
    a display;
    a processor adapted to produce a B-mode image and M-mode images from the reception signal output from the ultrasound transducers and to control display on the display;
    a storage adapted to store the M-mode images produced by the processor; and
    an operating panel adapted to be used to implement operations,
    wherein the processor displays the B-mode image including a frame that indicates a region of interest on the display,
    wherein when a region of interest is set in the B-mode image through an operation of the operating panel, the processor produces a region-of-interest image which is a B-mode image showing the set region of interest enlarged and which includes a selection line that is movable in the azimuth direction through another operation of the operating panel, and further produces M-mode images of all of selectable positions in the azimuth direction of the region-of-interest image to store the M-mode images in the storage,
    wherein the processor displays the produced region-of-interest image and an M-mode image of a position in the azimuth direction associated with the selection line in the region-of-interest image on the display,
    wherein when the selection line in the region-of-interest image displayed on the display is moved in the azimuth direction through an operation of the operating panel, the processor reads out from the storage an M-mode image corresponding to a position in the azimuth direction associated with the moved selection line and displays the read-out M-mode image in place of the M-mode image being displayed on the display, and
    wherein the processor detects heartbeats for all the M-mode images stored in the storage, stores each of the detected heartbeats of each of all the M-mode images in the storage in association with each of all the M-mode images, and displays start positions and end positions of all of heartbeats in an M-mode image displayed on the display based on the detected heartbeats of all the M-mode images stored in the storage.

2. The ultrasound diagnostic apparatus according to claim 1,
    wherein when the processor selects one heartbeat from among heartbeats displayed in the M-mode image displayed on the display through an operation of the operating panel, the processor displays indications at a start position and an end position of the selected one heartbeat in the M-mode image to inform that the one heartbeat has been selected.

3. The ultrasound diagnostic apparatus according to claim 2,
    wherein when the processor adjusts a start position and/or an end position of the selected one heartbeat in the M-mode image through an operation of the operating panel,
    the processor changes the indication of the start position and/or the indication of the end position of the selected one heartbeat in the displayed M-mode image in accordance with adjustment of the start position and/or the end position of the selected one heartbeat.

4. The ultrasound diagnostic apparatus according to claim 1, wherein the processor increases a frame rate of ultrasonic waves transmitted by the ultrasound transducers in response to an instruction to set the region of interest to be higher than before the instruction to set the region of interest.

5. The ultrasound diagnostic apparatus according to claim 1, wherein when there is a failed portion in which the processor fails to detect a heartbeat in all the M-mode images, the processor displays a start position and an end position of a heartbeat in the failed portion based on intervals of the detected heartbeats around the failed portion.

* * * * *